(12) United States Patent
Duffy et al.

(10) Patent No.: US 10,368,989 B2
(45) Date of Patent: Aug. 6, 2019

(54) HINGED TRANSCATHETER PROSTHETIC HEART VALVE DELIVERY SYSTEM

(71) Applicant: Medtronic Vascular Galway, Ballybrit, Galway (IE)

(72) Inventors: Niall Duffy, Ballybrit (IE); Marian Creaven, Ballybrit (IE)

(73) Assignee: Medtronic Vascular Galway (IE)

(*) Notice: Subject to any disclaimer, the term of this patent is extended or adjusted under 35 U.S.C. 154(b) by 503 days.

(21) Appl. No.: 14/681,893

(22) Filed: Apr. 8, 2015

(65) Prior Publication Data

US 2015/0297346 A1 Oct. 22, 2015

Related U.S. Application Data

(60) Provisional application No. 61/980,930, filed on Apr. 17, 2014.

(51) Int. Cl.
*A61F 2/24* (2006.01)
*A61M 25/01* (2006.01)

(52) U.S. Cl.
CPC ....... *A61F 2/2436* (2013.01); *A61M 25/0138* (2013.01); *A61F 2/2418* (2013.01); *A61M 25/0147* (2013.01)

(58) Field of Classification Search
CPC ........ A61F 2/2427; A61F 2/2436; A61F 2/95; A61F 2/962; A61F 2/966; A61M 25/0138; A61M 25/0147
See application file for complete search history.

(56) References Cited

U.S. PATENT DOCUMENTS

| | | | | |
|---|---|---|---|---|
| 5,042,707 A | * | 8/1991 | Taheri | A61B 17/0684 227/175.1 |
| 5,448,989 A | * | 9/1995 | Heckele | A61B 1/0055 600/104 |
| 2004/0138529 A1 | * | 7/2004 | Wiltshire | A61B 1/0055 600/144 |
| 2005/0043711 A1 | | 2/2005 | Corcoran | |
| 2008/0188928 A1 | | 8/2008 | Salahieh | |
| 2011/0207999 A1 | * | 8/2011 | Torisawa | A61B 1/00078 600/114 |

(Continued)

FOREIGN PATENT DOCUMENTS

| GB | 2433700 | 7/2007 |
|---|---|---|
| WO | WO2006/039646 | 4/2006 |

(Continued)

OTHER PUBLICATIONS

PCT/US2015/02498, The International Search Report and the Written Opinion of the International Searching Authority, dated Jun. 18, 2015.

(Continued)

*Primary Examiner* — Ryan J. Severson
*Assistant Examiner* — Christian D. Knauss

(57) ABSTRACT

A machined or molded hinge design, for use with a delivery device, which allows for controlled deflection of a large diameter catheter. With embodiments in which the delivery device is employed to implant a prosthetic heart valve, deflection of the catheter allows for central alignment of the delivery system in the native annulus during deployment of the bioprosthesis.

16 Claims, 12 Drawing Sheets

(56) References Cited

U.S. PATENT DOCUMENTS

2012/0239142 A1* 9/2012 Liu .................. A61F 2/0095
              623/2.11
2014/0222142 A1  8/2014 Kovalsky
2014/0277403 A1  9/2014 Peter

FOREIGN PATENT DOCUMENTS

| WO | WO2006/076890 | 7/2006 |
| WO | WO2007/149841 | 12/2007 |
| WO | WO2011/035327 | 3/2011 |
| WO | WO2012/116368 | 8/2012 |

OTHER PUBLICATIONS

CN Counterpart Appln. No. 201580019650.3 1st Office Action—China dated Oct. 20, 2017.
CN Counterpart Appln. No. 201580019650.3 2nd Office Action—China dated Jun. 4, 2018, CN Appln. No. 201580019650.3.

* cited by examiner

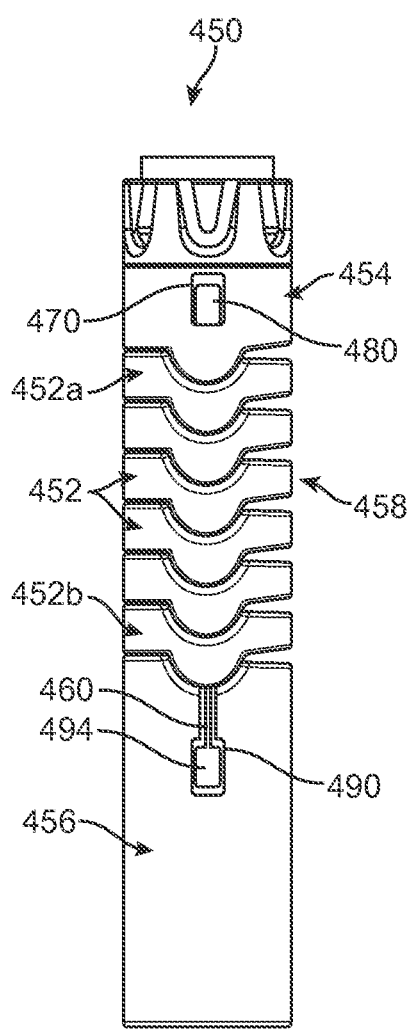
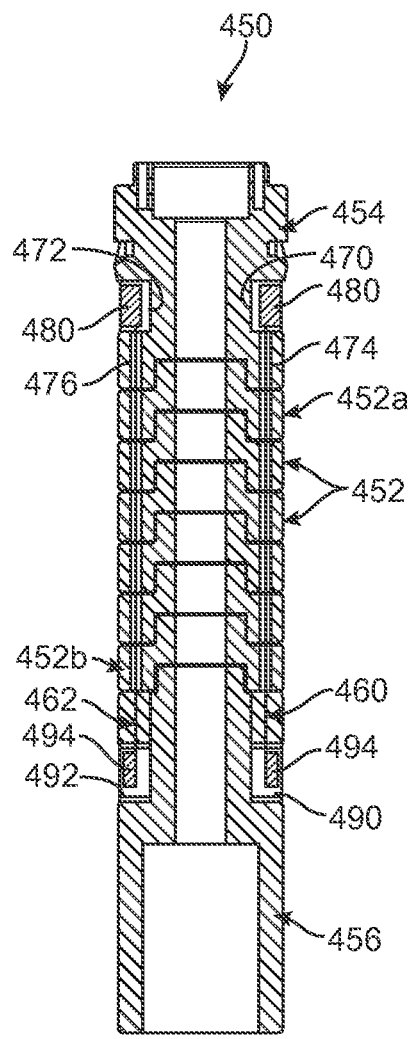
FIG. 10A                FIG. 10B
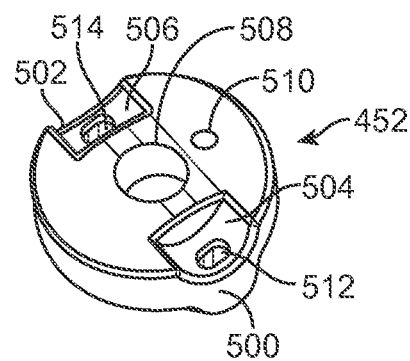
FIG. 10C

HINGED TRANSCATHETER PROSTHETIC HEART VALVE DELIVERY SYSTEM

CROSS REFERENCE TO RELATED APPLICATIONS

This Non-Provisional patent application claims the benefit of the filing date of U.S. Provisional Patent Application Ser. No. 61/980,930, filed Apr. 17, 2014, entitled "HINGED TRANSCATHETER PROSTHETIC HEART VALVE DELIVERY SYSTEM," which is herein incorporated by reference.

BACKGROUND

The present disclosure relates to delivery devices for implanting transcatheter valves. More particularly, it relates to catheter-based devices with controlled deflection for implanting a prosthetic heart valve.

A human heart includes four heart valves that determine the pathway of blood flow through the heart: the mitral valve, the tricuspid valve, the aortic valve, and the pulmonary valve. The mitral and tricuspid valves are atrio-ventricular valves, which are between the atria and the ventricles, while the aortic and pulmonary valves are semilunar valves, which are in the arteries leaving the heart. Ideally, native leaflets of a heart valve move apart from each other when the valve is in an open position, and meet or "coapt" when the valve is in a closed position. Problems that may develop with valves include stenosis in which a valve does not open properly, and/or insufficiency or regurgitation in which a valve does not close properly. Stenosis and insufficiency may occur concomitantly in the same valve. The effects of valvular dysfunction vary, with regurgitation or backflow typically having relatively severe physiological consequences to the patient.

Diseased or otherwise deficient heart valves can be repaired or replaced using a variety of different types of heart valve surgeries. One conventional technique involves an open-heart surgical approach that is conducted under general anesthesia, during which the heart is stopped and blood flow is controlled by a heart-lung bypass machine.

More recently, minimally invasive approaches have been developed to facilitate catheter-based implantation of the valve prosthesis on the beating heart, intending to obviate the need for the use of classical sternotomy and cardiopulmonary bypass. In general terms, an expandable prosthetic valve is compressed about or within a catheter, inserted inside a body lumen of the patient, such as the femoral artery, and delivered to a desired location in the heart.

The heart valve prosthesis employed with catheter-based, or transcatheter, procedures generally includes an expandable multi-level frame or stent that supports a valve structure having a plurality of leaflets. The frame can be contracted during percutaneous transluminal delivery, and expanded upon deployment at or within the native valve. One type of valve stent can be initially provided in an expanded or uncrimped condition, then crimped or compressed about a balloon portion of a catheter. The balloon is subsequently inflated to expand and deploy the prosthetic heart valve. With other stented prosthetic heart valve designs, the stent frame is formed to be self-expanding. With these systems, the valved stent is crimped down to a desired size and held in that compressed state within a sheath for transluminal delivery. Retracting the sheath from this valved stent allows the stent to self-expand to a larger diameter, fixating at the native valve site. In more general terms, then, once the prosthetic valve is positioned at the treatment site, for instance within an incompetent native valve, the stent frame structure may be expanded to hold the prosthetic valve firmly in place. One example of a stented prosthetic valve is disclosed in U.S. Pat. No. 5,957,949 to Leonhardt et al., which is incorporated by reference herein in its entirety.

The actual shape and configuration of any particular transcatheter prosthetic heart valve is dependent, at least to some extent, upon the valve being replaced or repaired (i.e., mitral valve, tricuspid valve, aortic valve, or pulmonary valve). The stent frame must oftentimes provide and maintain (e.g., elevated hoop strength and resistance to radially compressive forces) a relatively complex shape in order to achieve desired fixation with the corresponding native anatomy. Taken in combination, these design features can give rise to delivery obstacles. For example, when compressed and constrained within the delivery device's outer sheath capsule, a self-expanding stent frame will exert significant radial forces on the capsule. Thus, the capsule must have a robust construction, capable of statically resisting the applied force. However, the capsule, as well as other portions of the outer sheath, must also be sufficiently flexible to traverse the tortuous path leading to the native valve annulus site. As a point of reference, the preferred delivery approach oftentimes includes one or more significant bends or turns. In many instances, the native anatomy creates the "tight" or small radius of curvature bends; as the capsule (or other components of the delivery device) comes into atraumatic contact with the native anatomy, the native anatomy naturally assists in "forcing" the outer sheath (including the capsule) to the necessary shape. A retrograde approach to the aortic valve is but one example, where contact with the native anatomy assists in directing the delivery device about the significant curvature of the aortic arch.

With other procedures, however, it may be necessary to more directly steer the outer sheath. For example, the mitral valve is oftentimes approached at the left atrium via an opening in the atrial septum. Once located within the left atrium, the outer sheath must form a bend angle on the order of 45 degrees in order to position the capsule at the native mitral valve. Conventionally, a guide wire can be employed to direct or steer the delivery tool along the necessary path of curvature in achieving this desired orientation. Where the outer sheath has a bulked configuration, it can be difficult to effectuate the necessary bend with only the guide wire. Moreover, with some prosthetic mitral valve (as well as other prosthetic heart valve) designs, a greatly reduced size in the compressed state is not reasonably possible, meaning that the outer sheath will also have a relatively large diameter. A larger diameter sheath is more difficult to deflect or articulate over a smaller radius curve.

Although there have been multiple advances in transcatheter prosthetic heart valves and related delivery systems and techniques, there is a continuing need to provide different delivery tools for controlled delivery of the prosthesis to the native valve site.

SUMMARY

Some aspects of the present disclosure are directed toward a delivery device for a stented prosthetic heart valve. The delivery device includes an outer sheath, an inner shaft, a support shaft, and a deflection assembly. The inner shaft, the support shaft and the deflection assembly are slidably disposed within the outer sheath. The deflection assembly includes a hinge region interposed between the intermediate shaft and the support shaft. The deflection assembly includes a plurality of stacked hinge segments, a leading hub and a joiner hub. The plurality of hinge segments includes a proximal-most hinge segment and a distal-most hinge segment. The hinge segments are each discretely formed as a solid body, and have complimentary engagement features by which immediately adjacent ones of the hinge segments interface with, and can articulate relative to, one another. The joiner hub interfaces with the proximal-most hinge segment, and is connected to the inner shaft. The leading hub interfaces with the distal-most hinge segment, and is connected to the support shaft. The delivery device is configured to provide a loaded state in which a stented prosthetic heart valve is compressed over the support shaft and retained within a capsule of the outer sheath. The hinge region of the deflection assembly can be deflected by a user to change a spatial orientation of the support shaft relative to the intermediate shaft while the delivery device is in the loaded state.

BRIEF DESCRIPTION OF THE DRAWINGS

FIG. 10A is a side view of portions of another deflection assembly in accordance with principles of the present disclosure;

FIG. 10B is a cross-sectional view of the deflection assembly of FIG. 10A;

FIG. 10C is an enlarged perspective view of a hinge segment useful with the deflection assembly of FIG. 10A;

DETAILED DESCRIPTION

Figure 1A:
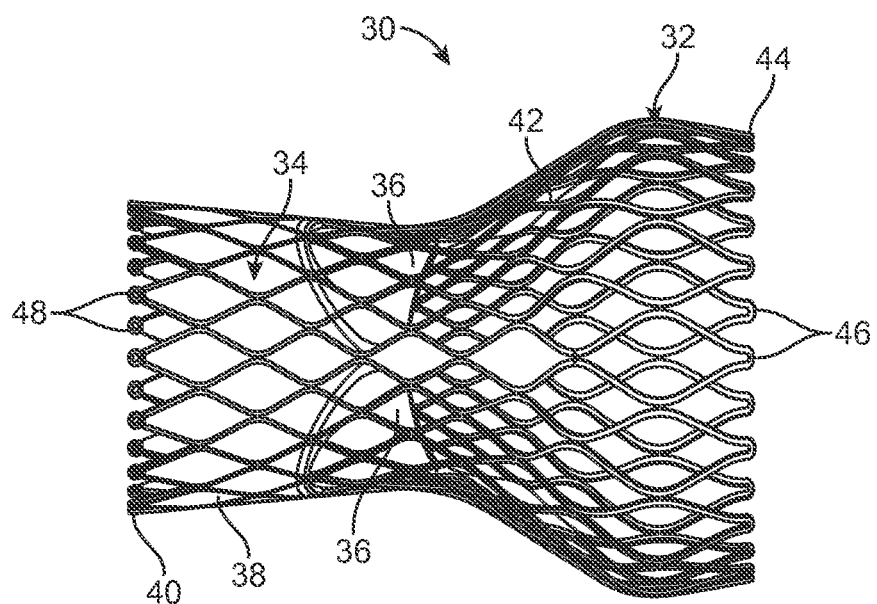
FIG. 1A is a side view of a stented prosthetic heart valve useful with systems, devices and methods of the present disclosure and in a normal, expanded condition.

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician. As used herein with reference to an implanted valve prosthesis, the terms "distal", "outlet", and "outflow" are understood to mean downstream to the direction of blood flow, and the terms "proximal", "inlet", or "inflow" are understood to mean upstream to the direction of blood flow. In addition, as used herein, the terms "outward" or "outwardly" refer to a position radially away from a longitudinal axis of a frame of the valve prosthesis and the terms "inward" or "inwardly" refer to a position radially toward a longitudinal axis of the frame of the valve prosthesis. As well the terms "backward" or "backwardly" refer to the relative transition from a downstream position to an upstream position and the terms "forward" or "forwardly" refer to the relative transition from an upstream position to a downstream position.

As referred to herein, stented transcatheter prosthetic heart valves useful with and/or as part of the various systems, devices and methods of the present disclosure may assume a wide variety of different configurations, such as a bioprosthetic heart valve having tissue leaflets or a synthetic heart valve having polymeric, metallic or tissue-engineered leaflets, and can be specifically configured for replacing any of the four valves of the human heart. Thus, the stented prosthetic heart valve useful with the systems, devices, and methods of the present disclosure can be generally used for replacement of a native aortic, mitral, pulmonic or tricuspid valve, or to replace a failed bioprosthesis, such as in the area of an aortic valve or mitral valve, for example.

In general terms, the stented prosthetic heart valves of the present disclosure include a stent or stent frame having an internal lumen maintaining a valve structure (tissue or synthetic), with the stent frame having a normal, expanded condition or arrangement and collapsible to a compressed condition or arrangement for loading within a delivery device. The stent frame is normally constructed to self-deploy or self-expand when released from the delivery device. For example, the stents or stent frames are support structures that comprise a number of struts or wire segments arranged relative to each other to provide a desired compressibility and strength to the prosthetic heart valve. The struts or wire segments are arranged such that they are capable of self-transitioning from a compressed or collapsed condition to a normal, radially expanded condition. The struts or wire segments can be formed from a shape memory material, such as a nickel titanium alloy (e.g., Nitinol™). The stent frame can be laser-cut from a single piece of material, or can be assembled from a number of discrete components.

Figure 1B:
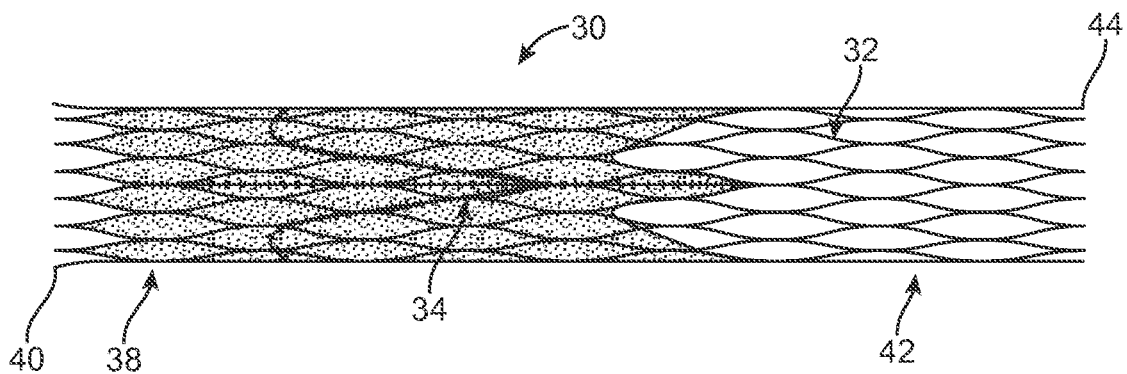
FIG. 1B is a side view of the prosthetic heart valve of FIG. 1A in a compressed condition.

With the above understanding in mind, one simplified, non-limiting example of a stented prosthetic heart valve 30 useful with systems, devices and methods of the present disclosure is illustrated in FIG. 1A. As a point of reference, the prosthetic heart valve 30 is shown in a normal or expanded condition in the view of FIG. 1A; FIG. 1B illustrates the prosthetic heart valve in a compressed condition (e.g., when compressively retained within an outer catheter or sheath as described below). The prosthetic heart valve 30 includes a stent or stent frame 32 and a valve structure 34. The stent frame 32 can assume any of the forms mentioned above, and is generally constructed so as to be self-expandable from the compressed condition (FIG. 1B) to the normal, expanded condition (FIG. 1A).

The valve structure 34 can assume a variety of forms, and can be formed, for example, from one or more biocompatible synthetic materials, synthetic polymers, autograft tissue, homograft tissue, xenograft tissue, or one or more other suitable materials. In some embodiments, the valve structure 34 can be formed, for example, from bovine, porcine, equine, ovine and/or other suitable animal tissues. In some embodiments, the valve structure 34 can be formed, for example, from heart valve tissue, pericardium, and/or other suitable tissue. In some embodiments, the valve structure 34 can include or form one or more leaflets 36. For example, the valve structure 34 can be in the form of a tri-leaflet bovine pericardium valve, a bi-leaflet valve, or another suitable valve. In some constructions, the valve structure 34 can comprise two or three leaflets that are fastened together at enlarged lateral end regions to form commissural joints, with the unattached edges forming coaptation edges of the valve structure 34. The leaflets 36 can be fastened to a skirt that in turn is attached to the frame 32. The upper ends of the commissure points can define an inflow portion 38 corresponding to a first or inflow end 40 of the prosthesis 30. The opposite end of the valve can define an outflow portion 42 corresponding to a second or outflow end 44 of the prosthesis 30. As shown, the stent frame 32 can have a lattice or cell-like structure, and optionally forms or provides crowns 46 and/or eyelets 48 (or other shapes) at the outflow and inflow ends 40, 44.

Figure 2:
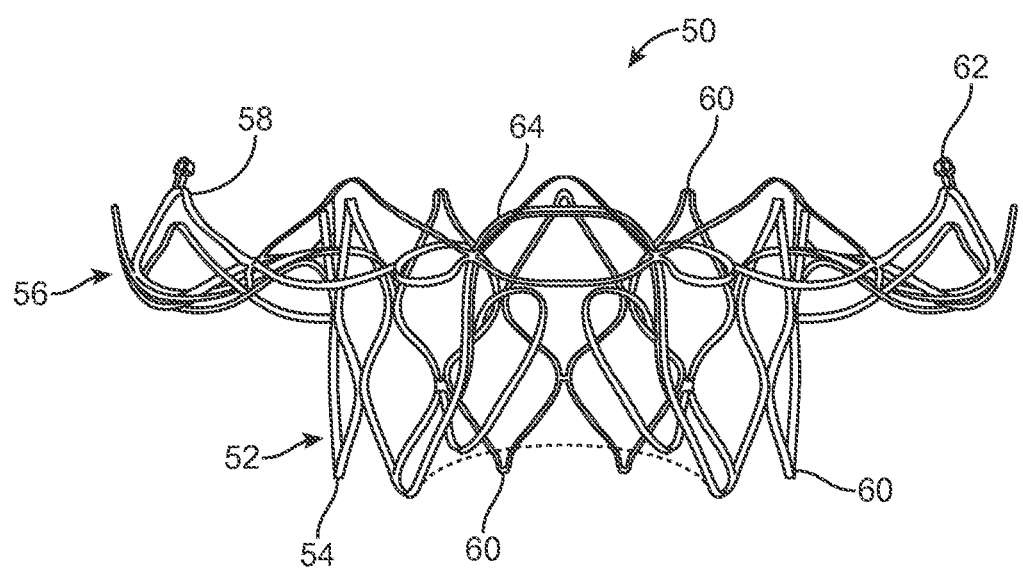
FIG. 2 is a side view of another exemplary prosthetic heart valve stent useful with systems, devices and methods of the present disclosure and in a normal, expanded condition.

With the one exemplary construction of FIGS. 1A and 1B, the prosthetic heart valve 30 can be configured (e.g., sized and shaped) for replacing or repairing an aortic valve. Alternatively, other shapes are also envisioned, adapted to mimic the specific anatomy of the valve to be repaired (e.g., stented prosthetic heart valves useful with the present disclosure can alternatively be shaped and/or sized for replacing a native mitral, pulmonic or tricuspid valve). For example, FIG. 2 illustrates another non-limiting example of a stent frame 50 portion of another prosthetic heart valve with which the systems, devices and methods of the present disclosure are useful. In the normal or expanded condition of FIG. 2, the stent frame 50 can be sized and shaped for mitral valve implantation. Though not shown, the valve structure attached to the stent frame 50 defines an outflow portion 52 arranged at a first or outflow end 54, and an inflow portion 56 arranged at a second or inflow end 58. As compared to the stent frame 32 of FIG. 1A, the inflow portion 56 can exhibit a more pronounced change in shape relative to the corresponding outflow portion 52. Regardless, the stent frame 50 can be forced and constrained to a compressed condition (not shown, but akin to the shape of FIG. 1A) during delivery, and will self-expand to the natural condition of FIG. 2 upon removal of the constraining force(s). As a point of reference, in some constructions, the stent frame 50 is configured to be crimped to a diameter on the order of 12 mm during delivery, and will self-expand to the natural, expanded condition that includes the inflow portion 56 having a diameter on the order of 60 mm. As reflected in FIG. 2, crowns 60 and/or eyelets 62 (or other shapes) optionally can be formed at one or both of the outflow and inflow ends 54, 58. Further, the stent frame 50 can optionally include or carry additional structural components, such as support arm(s) 64.

Figure 3A:
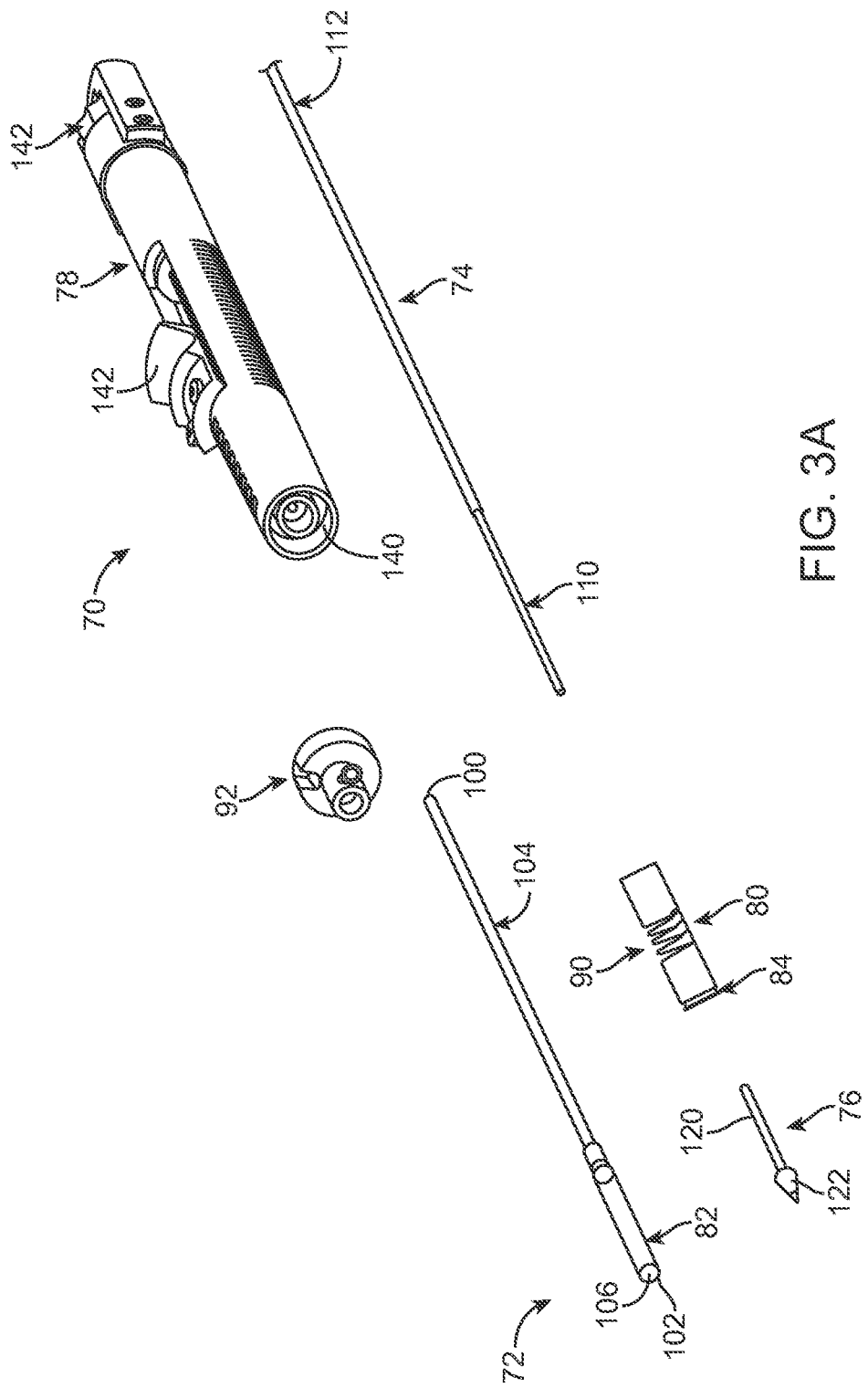
FIG. 3A is an exploded perspective view of a stented prosthetic heart valve delivery device in accordance with principles of the present disclosure.
Figure 3B:
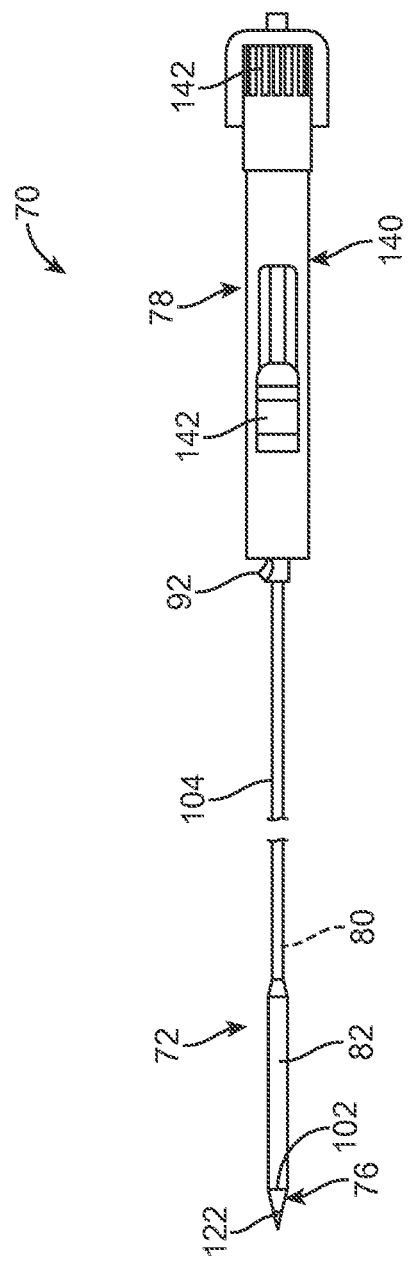
FIG. 3B is a side view of the delivery device of FIG. 3A.

With the above understanding of the stented prosthetic heart valves in mind, one embodiment of a delivery device 70 for percutaneously delivering the prosthesis is shown in simplified form in FIGS. 3A and 3B. The delivery device 70 includes a delivery sheath assembly 72, an inner shaft assembly 74, an inner support assembly 76, a handle assembly 78, and a deflection assembly 80. Details on the various components are provided below. In general terms, however, the delivery device 70 combines with a stented prosthetic heart valve (not shown) to form a system for performing a therapeutic procedure on a defective heart valve of a patient. The delivery device 70 provides a loaded or delivery state in which a stented prosthetic heart valve is loaded over the inner support assembly 76 and is compressively retained within a capsule 82 of the delivery sheath assembly 72. For example, the deflection assembly 80 (or the support assembly 76) can include or provide a valve retainer 84 configured to selectively receive a corresponding feature (e.g., posts) provided with the prosthetic heart valve stent frame. The delivery sheath assembly 72 can be manipulated to withdraw the capsule 82 proximally from over the prosthetic heart valve via operation of the handle assembly 78, permitting the prosthesis to self-expand and partially release from the inner support assembly 76. When the capsule 82 is refracted proximally beyond the valve retainer 84, the stented prosthetic heart valve can completely release or deploy from the delivery device 70. The delivery device 70 can optionally include other components that assist or facilitate or control complete deployment. Regardless, the deflection assembly 80 includes a hinge region 90. As described below, the hinge region 90 is operable to deflect or bend the corresponding segment of the delivery sheath assembly 72 (otherwise disposed over the hinge region 90) in a controlled fashion, effectuating a change in spatial orientation of the inner support assembly 76 (and thus the prosthesis and the capsule 82 when disposed over the inner support assembly 76) relative to the inner shaft assembly 74 and the handle assembly 78.

Various features of the components 72-78 reflected in FIGS. 3A and 3B and as described below can be modified or replaced with differing structures and/or mechanisms. Thus, the present disclosure is in no way limited to the delivery sheath assembly 72, the inner shaft assembly 74, the support assembly 76 or the handle assembly 78 as shown and described below. Any construction that generally facilitates compressed loading of a stented prosthetic heart valve over an inner shaft via a retractable outer sheath or capsule is acceptable. Further, the delivery device 70 can optionally include additional components or features, such as a flush port assembly 92, a recapture sheath (not shown), etc.

In some embodiments, the delivery sheath assembly 72 defines proximal and distal ends 100, 102, and includes the capsule 82 and an outer shaft 104. The delivery sheath assembly 72 can be akin to a catheter, defining a lumen 106 (referenced generally) that extends from the distal end 102 through the capsule 82 and at least a portion of the outer shaft 104. The lumen 106 can be open at the proximal end 100 (e.g., the outer shaft 104 can be a tube). The capsule 82 extends distally from the outer shaft 104, and in some embodiments has a more stiffened construction (as compared to a stiffness of the outer shaft 104) that exhibits sufficient radial or circumferential rigidity to overtly resist the expected expansive forces of the stented prosthetic heart valve (not shown) when compressed within the capsule 82. For example, the outer shaft 104 can be a polymer tube embedded with a metal braiding, whereas the capsule 82 includes a laser-cut metal tube that is optionally embedded within a polymer covering. Alternatively, the capsule 82 and the out shaft 104 can have a more uniform or even homogenous construction (e.g., a continuous polymer tube). Regardless, the capsule 82 is constructed to compressively retain the stented prosthetic heart valve at a predetermined diameter when loaded within the capsule 82, and the outer shaft 104 serves to connect the capsule 82 with the handle assembly 78. The outer shaft 104 (as well as the capsule 82) is constructed to be sufficiently flexible for passage through a patient's vasculature, yet exhibits sufficient longitudinal rigidity to effectuate desired axial movement of the capsule 82. In other words, proximal retraction of the outer shaft 104 is directly transferred to the capsule 82 and causes a corresponding proximal retraction of the capsule 82. In other embodiments, the outer shaft 104 is further configured to transmit a rotational force or movement onto the capsule 82.

The inner shaft assembly 74 can have various constructions appropriate for supporting the delivery sheath assembly 72, including indirectly supporting the inner support assembly 76 (and a stented prosthetic heart valve disposed thereon) relative to the capsule 82. In some embodiments, the inner shaft assembly 74 includes an intermediate shaft or tube 110 and a proximal shaft or tube 112. The intermediate tube 110 is optionally formed of a flexible polymer material (e.g., PEEK), and is sized to be slidably received within the delivery sheath assembly 72. The intermediate tube 110 serves as a transition to the deflection assembly 80, and in some embodiments is a flexible polymer tubing (e.g., PEEK) having a diameter slightly less than that of the proximal tube 112. The proximal tube 112 can have a more rigid construction, configured for robust assembly with the handle assembly 78, such as a metal hypotube. Other constructions are also envisioned. For example, in other embodiments, the intermediate and proximal tubes 110, 112 are integrally formed as a single, homogenous tube or shaft. Regardless, the inner shaft assembly 74 forms or defines at least one lumen (not shown) sized, for example, to slidably receive a guide wire (not shown). In other embodiments, the inner shaft assembly 74 can optionally form one or more additional lumens corresponding with one or more pull wire lumens provided with the deflection assembly 80 as described below.

The inner support assembly 76 includes an inner support shaft 120 and a tip 122. The inner support shaft 120 is sized to be slidably received within the lumen 106 of the delivery sheath assembly 72, and is configured for mounting to the deflection assembly 80. The inner support shaft 120 can be a flexible polymer tube embedded with a metal braid. Other constructions are also acceptable so long as the inner support shaft 120 exhibits sufficient structural integrity to support a loaded, compressed stented prosthetic heart valve (not shown). The tip 122 forms or defines a nose cone having a distally tapering outer surface adapted to promote atraumatic contact with bodily tissue. The tip 122 can be fixed or slidable relative to the inner support shaft 120. The inner support assembly 76 can define a continuous lumen (not shown) sized to slidably receive an auxiliary component such as a guide wire (not shown).

The handle assembly 78 generally includes a housing 140 and one or more actuator mechanisms 142 (referenced generally). The housing 140 maintains the actuator mechanism(s) 142, with the handle assembly 78 configured to facilitate sliding movement of the delivery sheath assembly 72 relative to other components (e.g., the inner shaft assembly 74, the support shaft assembly 76 and the deflection assembly 80). Further, one or more of the actuator mechanisms 142 interfaces with, or is considered part of, the deflection assembly 80 and is operable by a user to effectuate bending or deflection of the hinge region 90 as described below. The housing 140 can have any shape or size appropriate for convenient handling by a user.

Figure 4:
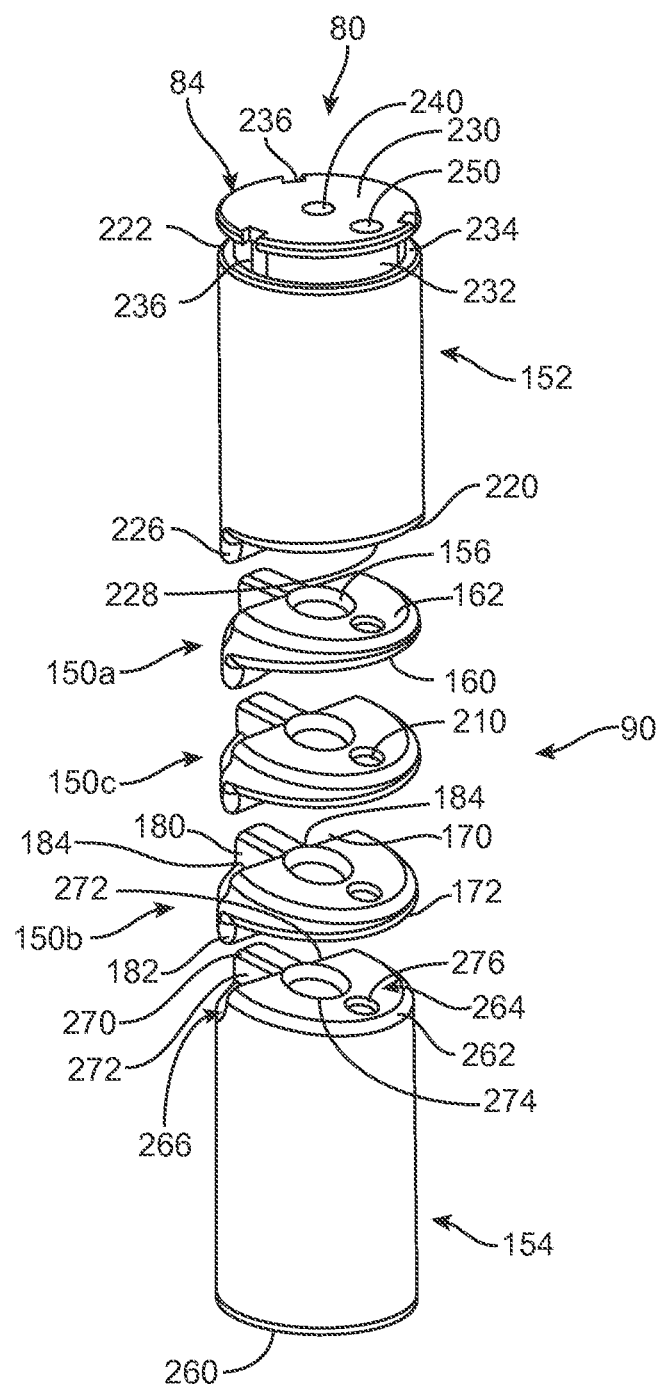
FIG. 4 is an exploded perspective view of portions of a deflection assembly in accordance with principles of the present disclosure and useful with the delivery device of FIG. 3A.

With the above general explanations of exemplary embodiments of the components 72-78 in mind, portions of one embodiment of the deflection assembly 80 are shown in greater detail in FIG. 4. The deflection assembly 80 includes a plurality of hinge segments 150, a leading hub 152 and a joiner hub 154. In general terms, leading hub 152 can form or be connected to the valve retainer 84 that is otherwise configured to selectively engage with corresponding features of the stented prosthetic heart valve. The joiner hub 154 is configured for attachment to the inner shaft assembly 74 (FIG. 3A). The hinge segments 150 are disposed between the leading hub 152 and the joiner hub 154, are can be articulated relative one another via tensioning of a pull wire (not shown) in establishing the hinge region 90.

While FIG. 4 illustrates the deflection assembly 80 as including three of the hinge segments 150, any other number, greater or lesser, is also acceptable. In more general terms, the deflection assembly 80 includes a distal-most hinge segment 150a, a proximal-most hinge segment 150b, and one or more intermediate hinge segments 150c. The hinge segments 150 can assume a variety of forms, and in some embodiments are identical. Each of the hinge segments 150 can be a generally disc-shaped body, and defines a central bore 156. With additional reference to FIG. 5A and as labeled for various ones of the hinge segments 150a-150c, the hinge segment 150 further includes or defines opposing, proximal and distal major surfaces 160, 162 along with a platform region 164 and a capture region 166. The platform region 164 tapers in thickness from the capture region 166, extending from a pivot side or edge 170 to a clearance side or edge 172. The pivot edge 170 is proximate the capture region 166 whereas the clearance edge 172 is opposite the capture region 166. The major surfaces 160, 162 can be substantially flat or planar along the platform region 164, although the planes of the major surfaces 160, 162 are not parallel.

The capture region 166 of each hinge segment 150 forms complimentary features for engaging with corresponding features of other ones of the hinge segments 150. For example, the capture region 166 can form a spine 180 and opposing tabs 182 (one of which is visible in the views). The spine 180 represents a continuation of the distal major surface 162 from the platform region 164, whereas the tabs 182 are defined as projections in the proximal major surface 160 from the platform region 164. Grooves 184 are formed at opposite sides of the spine 180, with each groove 184 being aligned with a corresponding one of the tabs 182. The grooves 184 represent a recess in the distal major surface 162. Similarly, a slot (hidden in the views) is formed between the tabs 182, aligned with the spine 180. The slot represents a recess in the proximal major surface 162.

Figure 5A:
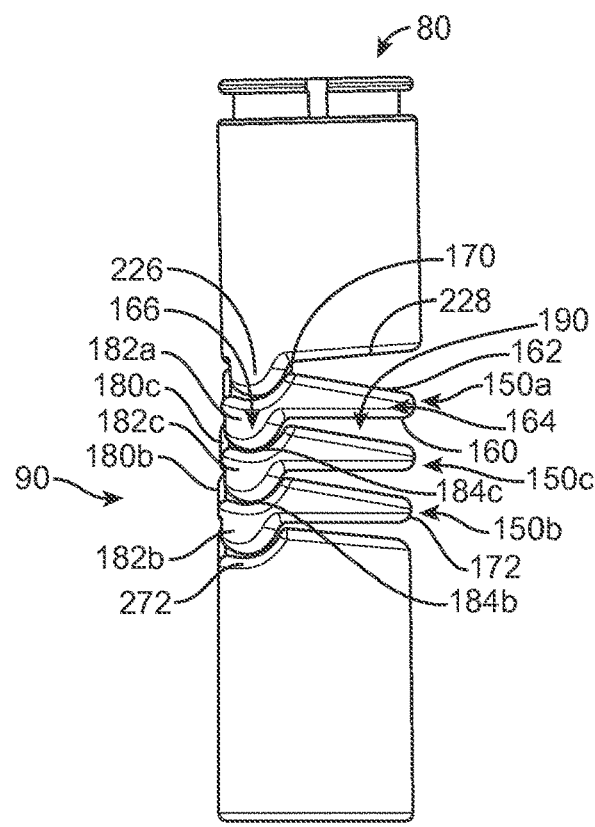
FIG. 5A is a side view of the deflection assembly of FIG. 4 upon final construction and in a linear arrangement.

Upon final assembly with the hinge segments 150 aligned and sequentially arranged (e.g., stacked), the grooves 184 are each sized and shaped to receive a respective one of the tabs 182 of an identically formed hinge segment 150. The slot is sized and shaped to receive the spine 180 of an identically formed hinge segment 150. For example, as shown in FIG. 5A one of the tabs 182c of the intermediate hinge segment 150c nests within a corresponding one of the grooves 184b of the proximal-most hinge segment 150b. Similarly, one of the tabs 182a of the distal-most hinge segment 150a nests within a corresponding one of the grooves 184c of the intermediate hinge segment 150c. Though primarily hidden in the view of FIG. 5A, the spine 180c of the intermediate hinge segment 150c nests within the slot of the distal-most hinge segment 150a, and the spine 180b of the proximal-most hinge segment 150b nests within the slot of the intermediate hinge segment 150c.

Figure 5B:
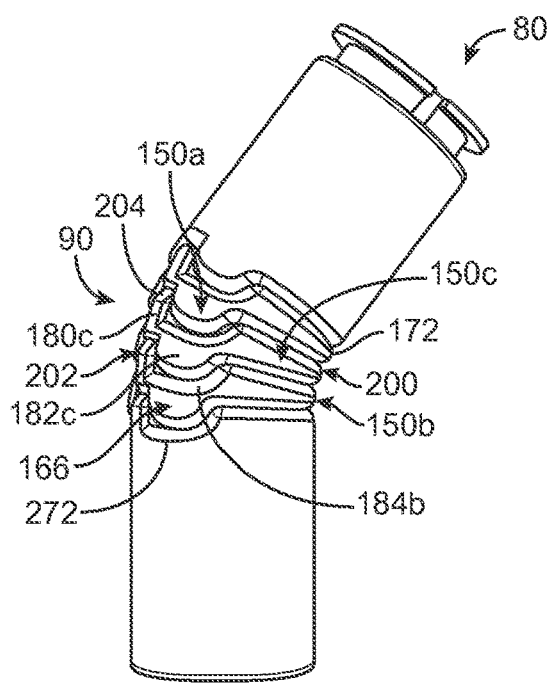
FIG. 5B is a side view of the deflection assembly of FIG. 5A in a deflected arrangement.

Upon final assembly, the central bores 156 (FIG. 4) are aligned to permit passage of an object, such as a guide wire (not shown). Further, in the assembled, linear arrangement of FIG. 5A, a clearance gap 190 is established between the hinge segments 150a-150c along the platform regions 164. Due to the tapered shape of the platform regions 164, a size of the gaps 190 increases toward the corresponding clearance edges 172. When the hinge segments 150a-150c are subjected to a tensioning force adjacent the clearance edges 172, the hinge segments 150a-150c are caused to articulate relative to one another, with each hinge segment 150a-150c pivoting relative to the immediately adjacent hinge segment 150a-150c at the pivot edges 170. As a result, the hinge region 90 collectively defined by the hinge segments 150a-150c deflects or forms a bend, as shown in FIG. 5B. This collective deflection or articulation can continue until the platform regions 164 are forced into contact with one another. In the deflected arrangement of FIG. 5B, then, the hinge region 90 is deflected to form a bend or curve having an interior curve or radius 200 (referenced generally) and an exterior curve or radius 202 (referenced generally). The interior curve 200 is collectively defined by the clearance edges 172. The exterior curve 202 is collectively defined by the capture regions 166. As shown, while the capture regions 166 will articulate relative to, and slightly separate from, one another as the hinge region 90 deflects or articulates, the hinge segments 150a-150c remain robustly engaged via the complimentary features of the capture regions 166 (e.g., FIGS. 5A and 5B illustrate that the tab 182c of the intermediate hinge segment 150c slides within, but remains nested with, the corresponding groove 184b of the proximal-most hinge segment 150b; the spine 180c of the intermediate hinge segment 150c slides within, but remains nested with, the slot (referenced generally at 204) of the distal-most hinge segment 150a; etc.). When the applied tension is reduced or overcome by other forces, the hinge region 90 can readily be reverted back from the deflected arrangement of FIG. 5B to the linear arrangement of FIG. 5A.

The deflection-causing tension can be applied to the hinge region 90 in a variety of manners. In some embodiments, the deflection assembly 80 includes one or more pull wires (not shown). For example, and returning to FIG. 4, each of the hinge segments 150 can define a pull wire lumen 210 adjacent the corresponding clearance edge 172 (e.g., between the central bore 156 and the clearance edge 172). The pull wire lumen 210 is open to the opposing major faces 160, 162, and is sized to slidably receive a pull wire (e.g., a small diameter wire, braided string, etc.). The pull wire is selected to be highly robust, capable of maintaining its structural integrity at the expected forces encountered during use (e.g., 150 N). Other constructions (e.g., multiple pull wires, etc.) are also acceptable.

The leading hub 152 is a generally cylindrical body (with an outer diameter generally corresponding with that of each of the hinge segments 150) defining a trailing side 220 opposite a leading side 222. The trailing side 220 is configured to interface with the distal-most hinge segment 150a in an articulating manner akin to the articulating interface between immediately adjacent ones of the hinge segments 150 as described above. Thus, in some embodiments, the trailing side 220 includes or forms proximally-projecting tabs 226 (one of which is visible in FIG. 4) sized and shaped to nest within a corresponding one of the grooves 184 formed by the distal-most hinge segment 150a. Further, a slot (hidden in the view) is formed, configured to slidably receive the spine 180 of the distal-most hinge segment 150a. A trailing face 228 (referenced generally) of the leading hub 152 is substantially planar for interfacing with the distal major surface 162 of the distal-most hinge segment 150a. With this configuration, the leading hub 152 effectively serves as a continuation of the hinge region 90, as reflected in FIGS. 5A and 5B.

The leading side 222 can assume various forms, and in some embodiments forms the valve retainer 84 (or portions thereof). The valve retainer 84 is generally configured in accordance with features of the stented prosthetic heart valve (and vice-versa), and is generally configured to assist in loading the prosthesis to the delivery device 70. For example, in some embodiments, the valve retainer 84, as formed by the leading hub 152, includes a head 230, a neck 232, and a shoulder 234. The neck 232 has a reduced diameter as compared to the head 230 and the shoulder 234, establishing a circumferential slot. Further, various axial slots 236 can be provided. The slots 236 are configured to temporarily receive and retain posts or other features provided by the stented prosthetic heart valve. A number of other valve retention configurations are equally acceptable, and the present disclosure is in no way limited to the valve retainer 84 as shown. Further, while the valve retainer 84 has been shown as being part of the leading hub 152, in other embodiments, the valve retainer 84 (or portions thereof) can be provided with other components of the delivery device apart from the leading hub 152.

The leading hub 152 can, in some embodiments, form a central bore 240 for slidably receiving a separate component, such as a guide wire (not shown). Upon final arrangement of the leading hub 152 relative to the hinge segments 150, the central bore 240 of the leading hub 152 is generally aligned with the central bore 156 of the distal-most hinge segment 150a for reasons made clear below. Further, the leading hub 152 can include or provide one or more features that facilitate assembly and/or operation of the mechanism utilized to apply deflection-causing tension on to the hinge region 90. For example, where the deflection assembly 80 incorporates one or more pull wires as described above, the leading hub 152 can define an axial pull wire lumen 250 at a location off-set from a center line of the leading hub 152. The pull wire lumen 250 of the leading hub 152 corresponds with the pull wire lumen 210 of each of the hinge segments 150. Upon final arrangement of the leading hub 152 relative to the hinge segments 150, the pull wire lumen 250 of the leading hub 152 is generally aligned with the pull wire lumen 210 of the distal-most hinge segment 150a such that a pull wire readily extends between the distal-most hinge segment 150a and the leading hub 152.

The joiner hub 154 is a generally cylindrical body (with an outer diameter generally corresponding with that of each of the hinge segments 150) defining a trailing side 260 opposite a leading side 262. The trailing side 260 is generally configured for assembly to another component of the delivery device 70, such as the intermediate shaft 110 (FIG. 3A). For example, the joiner hub 154 can form an internally-threaded hole (not shown) at the trailing side 260 that promotes threaded attachment with the intermediate shaft 110. Other connection techniques are equally acceptable.

The leading side 262 is configured to interface with the proximal-most hinge segment 150b in an articulating manner akin to the articulating interface between immediately adjacent ones of the hinge segments 150 as described above. Thus, in some embodiments, the leading side 262 includes or forms a platform region 264 and a capture region 266. A distal face of the platform region 264 is substantially planar for interfacing with the proximal major surface 150 of the proximal-most hinge segment 150b. The capture region 266 includes or provides a spine 270 located between opposing grooves 272. The spine 270 is configured to be slidably received within the slot (hidden) of the proximal-most hinge segment 150b. The grooves 272 are each sized and shaped to receive a corresponding one of the tabs 182 of the proximal-most hinge segment 150b in a nested fashion. With this configuration, the joiner hub 154 effectively serves as a continuation of the hinge region 90, as reflected in FIGS. 5A and 5B.

The joiner hub 154 can, in some embodiments, form a central bore 274 for slidably receiving a separate component, such as a guide wire (not shown). Upon final arrangement of the joiner hub 154 relative to the hinge segments 150, the central bore 274 of the joiner hub 154 is generally aligned with the central bore 156 of the proximal-most hinge segment 150b for reasons made clear below. Further, the joiner hub 154 can include or provide one or more features that facilitate assembly and/or operation of the mechanism utilized to apply deflection-causing tension on to the hinge region 90. For example, where the deflection assembly 80 incorporates one or more pull wires as described above, the joiner hub 154 can define an axial pull wire lumen 276 at a location off-set from a center line of the joiner hub 154. The pull wire lumen 276 of the joiner hub 154 corresponds with the pull wire lumen 210 of each of the hinge segments 150. Upon final arrangement of the joiner hub 154 relative to the hinge segments 150, the pull wire lumen 276 of the joiner hub 154 is generally aligned with the pull wire lumen 210 of the proximal-most hinge segment 150b such that a pull wire readily extends between the joiner hub 154 and the proximal-most hinge segment 150b.

The hinge segments 150, the leading hub 152, and the joiner hub 154 are, in some embodiments, formed of an identical or substantially identical material, such as a surgically safe plastic material. The hinge segments 150, the leading hub 152, and the joiner hub 154 are each formed as solid bodies, such as by a molding or machining process, with various features described above (e.g., tabs, grooves, spines, etc.) being molded or machined into the part. Regardless, each of the hinge segments 150 is discrete from one another, as well as from the leading hub 152 and the joiner hub 154. That is to say, the components 150-154 of the deflection assembly 80 are each a solid body, are not hollow, and are not commonly formed from a homogenous tube (e.g., the components 150-154 are not cut (for example, laser cut) from a single metal tube).

As alluded to above, final construction of the deflection assembly 80 is shown in FIG. 5A (it being understood that the optional pull wire(s) is omitted from the view). The joiner hub 154, the hinge segments 150, and leading hub 152 are longitudinally arranged or aligned in a sequential or stacked fashion. Adjacent ones of the hinge segments 150 are connected so as to permit articulating movement of each hinge segments 150 relative to one another as described above. A similar articulating interface is established between the leading hub 152 and the distal-most hinge segment 150a (e.g., the tabs 226 of the leading hub 152 nest within respective ones of the grooves 184 formed by the distal-most hinge segment 150a). A similar articulating interface is further established between the proximal-most hinge segment 150b and the joiner hub 154 (e.g., the tabs 182 of the proximal-most hinge segment 150b nest within respective ones of the grooves 272 of the joiner hub 154). As a result, the deflection assembly 80 can be readily transitioned between the linear arrangement of FIG. 5A and the deflected arrangement of FIG. 5B. With additional reference to FIG. 4, the central bores 156, 240, 274 are generally aligned with one another, such that an auxiliary component, such as a guide wire, can extend through the deflection assembly 80, with the auxiliary component being force to assume the shape of the hinge region 90 (i.e., when the deflection assembly 80 is deflected from the linear arrangement of FIG. 5A to the deflected arrangement of FIG. 5B, the guide wire or other auxiliary component extending through the central bores 156, 240, 274 will be forced to a similar shape, following a curvature collectively defined by the hinge region 90).

With embodiments in which one or more pull wires are provided with the deflection assembly 80 to facilitate user-prompted articulation between the linear and deflected arrangements, the pull wire (not shown) can be received through the pull wire lumens 210, 250, 276 as described above. Upon final assembly, the pull wire(s) extends proximally from the joiner hub 154, for example to the handle assembly 78 (FIGS. 3A and 3B), and is connected to a user actuator. A distal end of the pull wire(s) is rigidly connected to the leading hub 152 (e.g., the distal end of the pull wire extends through pull wire lumen 250 of the leading hub 152 and is held (e.g., via a knot or other coupling body) at the leading side 222). With this construction, a pulling or tensioning force applied to a proximal region of the pull wire(s) is transferred on to the leading hub 152, pulling or compressing the leading hub 152 toward the joiner hub 154 (that is otherwise held spatially stationary while tension is applied to the pull wire(s) via the inner shaft assembly 74 (FIG. 3A)). The hinge segments 150 are compressed toward one another between the hubs 152, 154 and articulate, allowing the hinge region 90 to articulate to the deflected arrangement of FIG. 5B.

Figure 6:
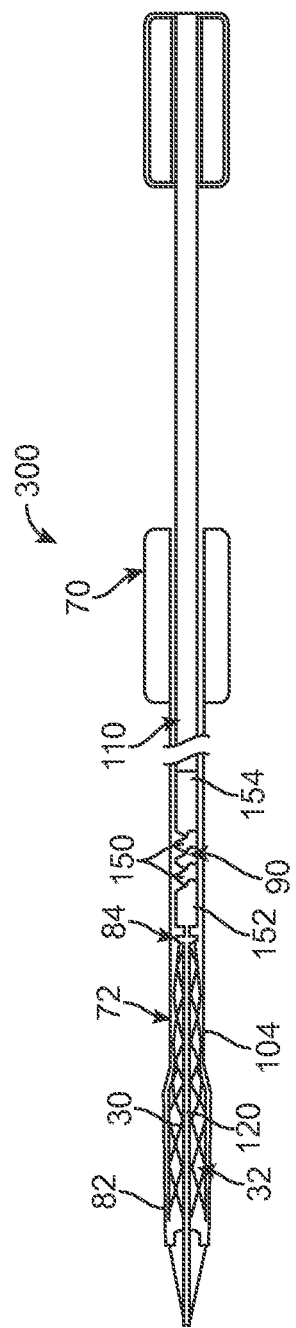
FIG. 6 is a simplified cross-sectional view of the delivery device of FIG. 3A loaded with a stented prosthetic heart valve.

The deflection assembly 80 is configured to be structurally robust such that any change in shape of the hinge region 90 is imparted on to any structure surrounding the hinge region 90. For example, a simplified representation of portions of the delivery device 70 in the delivery state and loaded with the stented prosthetic heart valve 30 (referenced generally) to provide a system 300 for performing a therapeutic procedure on a defective heart valve is shown in FIG. 6. For ease of illustration, only the stent frame 32 of the prosthesis 30 is depicted in FIG. 6. The stent frame 32 is crimped over the inner support shaft 120, and is compressibly held in the compressed condition by the capsule 82. Further, the stent frame 32 is connected to the valve retainer 84. The leading hub 152 is attached to the inner support shaft 120. The joiner hub 154 is attached to the intermediate shaft 110. As shown, the outer shaft 104 of the delivery sheath assembly 72 is coaxially received over the leading hub 152, the hinge segments 150, and the joiner hub 154. As the hinge region 90 is caused to deflect or articulate from the linear arrangement shown to a deflected arrangement (as in FIG.

5B, for example), the outer shaft 104 conforms to or with the deflected shape defined along the hinge region 90. Further, the leading hub 152 is spatially reoriented relative to the joiner hub 154; this movement, in turn, is transferred to the inner support shaft 120 and thus the prosthesis 30 carried thereon. As a result, articulation of the hinge region 90 spatially re-orients the prosthesis 30 (and all other components distal the hinge region 90) relative to joiner hub 154 and thus the intermediate shaft 110 (and all other components proximal the joiner hub 154). Notably, the deflection assemblies of the present disclosure are capable of generating the above-described deflection even when disposed within a relatively large delivery sheath or catheter, for example a delivery sheath or catheter having an inner diameter on the order of 12-13 mm.

Figure 7:
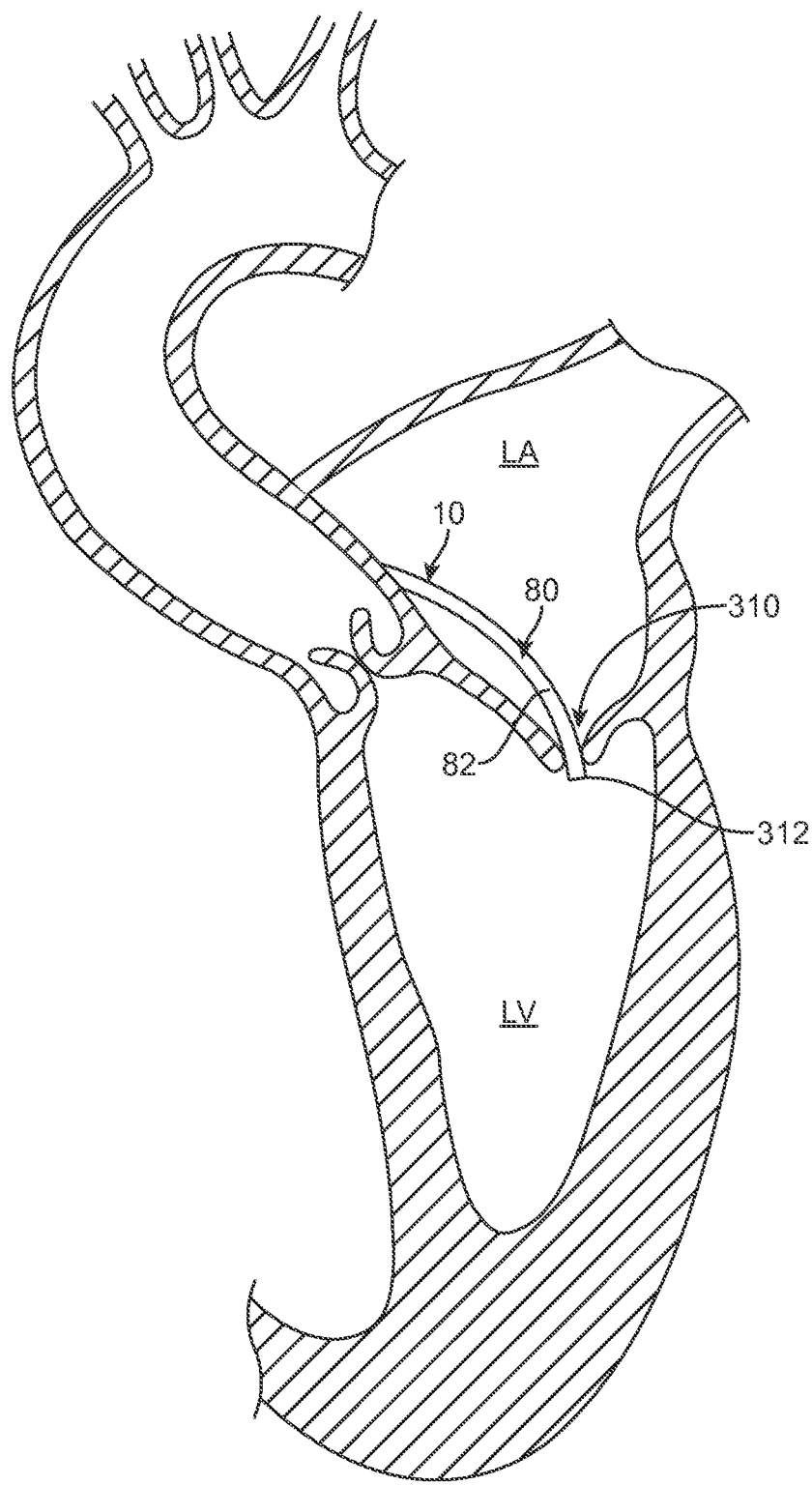
FIG. 7 illustrates a portion of a method of implanting a prosthetic heart valve at a mitral valve target location within a heart in accordance with principles of the present disclosure.

The delivery devices of the present disclosure can be used to deliver a number of different implantable articles to a various target sites in the human body. For example, FIG. 7 generally reflects use of the delivery device 70 in delivering a stented prosthetic heart valve (hidden) to a mitral valve target site 310. The mitral valve target site 310 separates the left atrium LA and the left ventricle LV. The delivery device 70 is shown after having been introduced into the vasculature via a percutaneous entry point (e.g., the Seldinger technique), and having been tracked through the vasculature and into the left atrium LA. For example, the percutaneous entry point may be formed in a femoral vein. Thereafter, a guide wire (not shown) is advanced through the circulatory system, eventually arriving at the heart. The guide wire is directed into the right atrium, traverses the right atrium and is made to puncture, with the aid of a transeptal needle or pre-existing hole, the atrial septum, thereby entering the left atrium LA. Once the guide wire is positioned, the endoluminal entry port and the atrial septum are dilated to permit entry of a guide catheter (not shown) and/or the delivery device 70 into the left atrium LA. Once in the left atrium LA, the deflection assembly 80 (referenced generally) is operated or caused to deflect to the deflected arrangement shown in FIG. 7, aligning a distal end 312 of the delivery device 70 with the mitral valve target site 310. Notably, the outer delivery sheath capsule 82 (as well as the stented prosthetic heart valve constrained therein) is caused to move to the aligned position with deflection of the deflection assembly 80.

Figure 8:
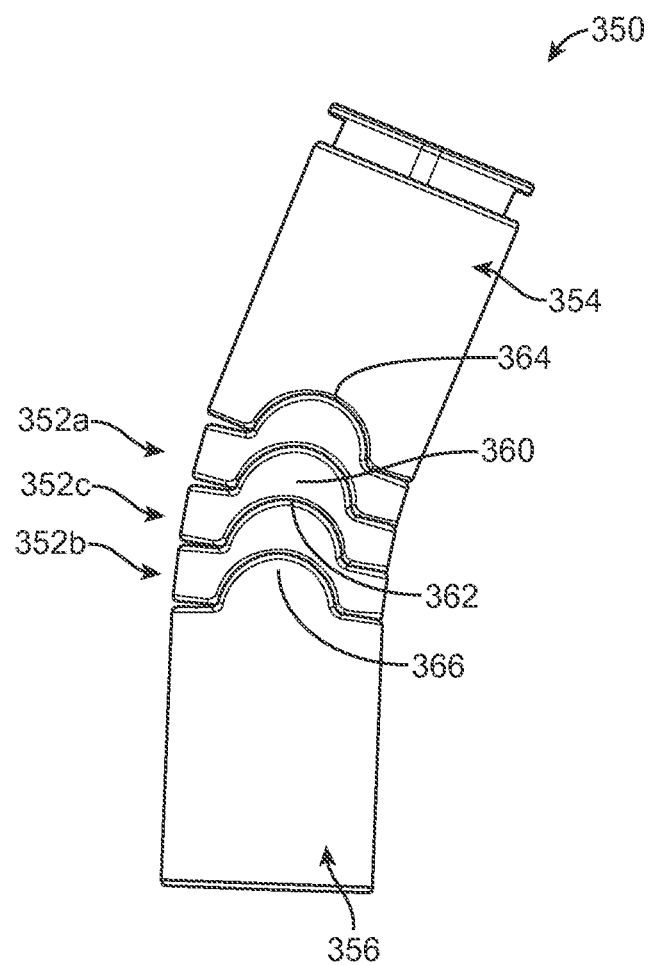
FIG. 8 is a side view of portions of another deflection assembly in accordance with principles of the present disclosure.

Although the deflection assembly 80 has been described as effecting an off-set hinge arrangement (e.g., the pivot point of the various assembly components relative to one another, for example the hinge segments 150 (FIG. 4), is off-set relative to an axial centerline), other constructions are also envisioned. For example, FIG. 8 is a simplified view of portions of another embodiment defection assembly 350 in accordance with principles of the present disclosure. The deflection assembly 350 includes a plurality of hinge segments 352, a leading hub 354, and a joiner hub 356. As tension-applying device (e.g., one or more pull wires) can also be included, but are omitted from the view for ease of illustration.

The hinge segments 352 can be highly akin to the hinge segments 150 (FIG. 4) described above, and generally include or form various complimentary features that promote an articulating interface between consecutively stacked or arranged ones of the hinge segments 352 (as well as between a distal-most hinge segment 352a and the leading hub 354, and between a proximal-most hinge segment 352b and the joiner hub 356). For example, each of the hinge segments 352 can include or form opposing tabs 360 (one of which is visible in FIG. 8) and opposing grooves 362 (one of which is visible in FIG. 8). The tabs 360 and the grooves 362 have a complimentary size and shape, such that the tab 360 of one hinge segment is slidably received or nested with a corresponding groove 362 of an immediately adjacent hinge segment 350. The leading hub 354 and the joiner hub 356 form or provide corresponding interface features (e.g., the leading hub 354 forms opposing grooves 364 (one of which is visible in FIG. 8) for receiving a corresponding one of the tabs 360 of the distal-most hinge segment 352a, whereas the joiner hub 356 forms or provides opposing tabs 366 (one of which is visible in FIG. 8) sized to slidably nest within a corresponding one of the grooves 362 of the proximal-most hinge segment 352b. Regardless, a hinged or articulating interface is established between adjacent ones of the components 352-356 upon final assembly, with the pivot point or line approximately intersecting an axial centerline of the corresponding component 352-356. In some embodiments, the off-set pivot arrangement (as in FIG. 4) may be desired where an increased lever effect is of interest.

Returning to FIG. 4, in some embodiments the hinge segments 150, the leading hub 152 and the joiner hub 154 can be generally maintained relative to one another by the pull wire(s) or other tension-applying mechanism. In other embodiments, the deflection assemblies of the present disclosure can include additional features that more directly join immediately adjacent ones of the components 150-154 relative to one another. As a point of reference, in some instances it may be desirable to limit separation of the components 150-156 relative to one another, for example when loading a stented prosthetic heart valve on to the delivery device 70. For example, and with additional reference to FIG. 6, one loading technique entails holding the stented prosthetic heart valve 30 in a compressed condition while the delivery sheath assembly 72 is moved distally to sequentially direct the capsule 82 over the prosthesis 30. Under these circumstances, a tension or pulling force will be applied on to the leading hub 152 (e.g., as the capsule 82 is moved distally, the capsule 82 will tend to apply a distal force on to the prosthesis 30, and thus on to the leading hub 152). Absent a more robust connection between the leading hub 152 and the distal-most hinge segment 150 (as well as between immediately adjacent ones of the hinge segments 150, and between the proximal-most hinge segment 150 and the joiner hub 154), the components 150-154 might undesirably separate from one another.

Figure 9A:
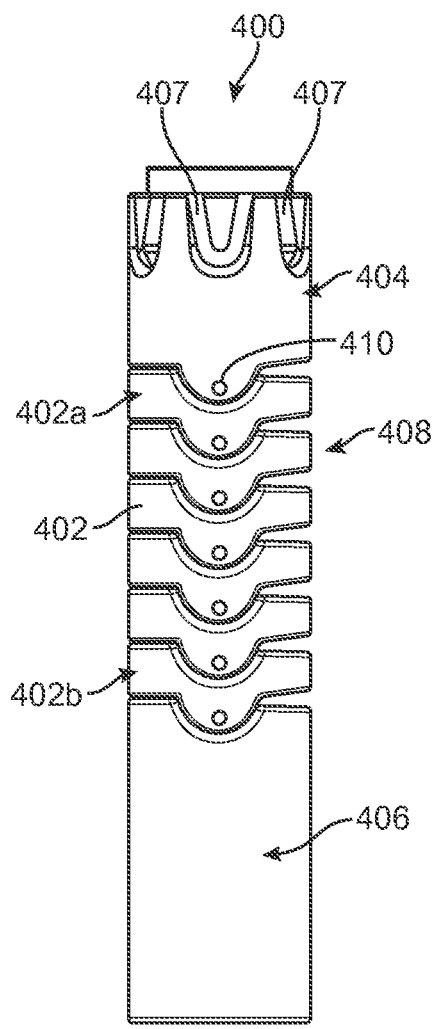
FIG. 9A is a side view of portions of another deflection assembly in accordance with principles of the present disclosure.
Figure 9B:
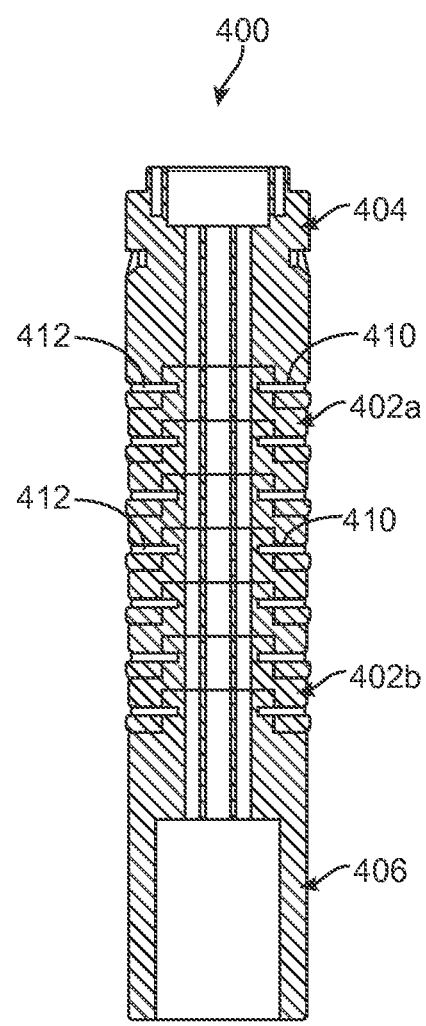
FIG. 9B is a cross-sectional view of the deflection assembly of FIG. 9A.

With the above in mind, portions of another embodiment deflection assembly 400 in accordance with principles of the present disclosure are shown in FIGS. 9A and 9B. The deflection assembly 400 includes a plurality of hinge segments 402, a leading hub 404, and a joiner hub 406. In general terms, the hinge segments 402 can be highly akin to the hinge segments 150 (FIG. 4), and can incorporate any of the features described above. Similarly, the leading hub 404 can be highly akin to the leading hub 152 (FIG. 4), and the joiner hub 406 can be highly akin to the joiner hub 154 (FIG. 4). The leading hub 404 can optionally form slots 407 for receiving respective components of a prosthetic heart valve (e.g., respective ones of the crowns 60 or eyelets 62 shown in FIG. 2). Regardless, an articulating interface is established between consecutive ones of the components 402-406 upon final assembly to collectively define a hinge region 408 as described above. In addition, the deflection assembly 400 includes one or more pins securing immediately adjacent ones of the components 402-406 to one another. For example, and as best shown in FIG. 9B, the leading hub 404 is connected to the distal-most hinge segment 402a by pins 410, 412. The pins 410, 412 are aligned with one another and arranged such that the leading hub 404 can articulate relative to the distal-most hinge segment 402a (and vice-versa), pivoting or rotating about the pins 410, 412. As shown, adjacent ones of the hinge segments 402 are similarly secured to one another by two pins 410, 412, respectively, as is the proximal-most hinge segment 402b to the joiner hub 406.

Figure 9C:
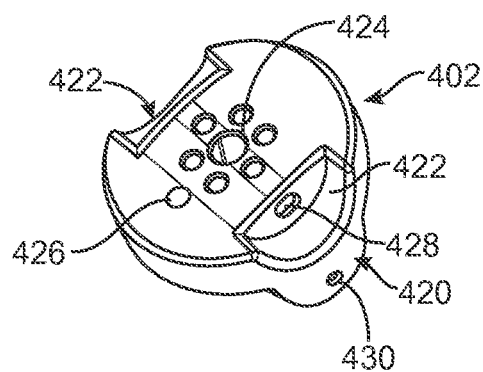
FIG. 9C is an enlarged perspective view of a hinge segment useful with the deflection assembly of FIG. 9A.

The pins 410, 412 can be assembled to the corresponding components 402-406 in a variety of manners. In some embodiments, the components 402-406 can be formed to define holes into which the pins 410, 412 are rotatably mounted. For example, FIG. 9C illustrates one of the hinge segments 402 in greater detail. Commensurate with previous descriptions, the hinge segment 402 can form or provide opposing tabs 420 (one of which is visible in the view) and opposing grooves 422. A central bore 424 is optionally provided, as is an optional pull wire lumen(s) 426. In addition, the hinge segment 402 forms a first hole 428 within or at each of the grooves 422, and a second hole 430 at or along each of the tabs 420 (it being understood that in the view of FIG. 9C, only one set of the holes 428, 430 is visible). Upon stacked arrangement of a first one of the hinge segments 402 to a second one of the hinge segments 402 (e.g., in which the tabs 420 of the first hinge segment 402 nest within the grooves 422 of the second hinge segment), corresponding ones of the holes 428, 430 will be aligned and can readily receive a corresponding one of the pins 410, 412 (FIG. 9B). The leading hub 404 and the joiner hub 406 can provide similar features or holes.

With the above construction, the hinge region 408 can articulate or deflect in accordance with previous descriptions (e.g., in response to a compressive force applied to the leading hub 404 in a direction of the joiner hub 406). Further, when placed in tension (e.g., a distal pulling force applied to the leading hub 404 while the joiner hub 406 is held stationary), the pins 410, 412 prevent the deflection assembly 400 from pulling apart.

Portions of another embodiment deflection assembly 450 in accordance with principles of the present disclosure are shown in FIGS. 10A and 10B. The deflection assembly 450 includes a plurality of hinge segment 452, a leading hub 454, and a joiner hub 456. In general terms, the hinge segments 452 can be highly akin to the hinge segments 150 (FIG. 4), and can incorporate any of the features described above. Similarly, the leading hub 454 can be highly akin to the leading hub 152 (FIG. 4), and the joiner hub 456 can be highly akin to the joiner hub 154 (FIG. 4). Thus, an articulating interface is established between consecutive ones of the components 452-456 upon final assembly to collectively define a hinge region 458 as described above. In addition, the deflection assembly 450 includes one or more wires securing immediately adjacent ones of the components 452-456 to one another.

For example, FIG. 10A, illustrates a first wire 460 extending between the leading hub 454 and the joiner hub 456, and interconnected with each of the hinge segments 452. As generally reflected by FIG. 10B, a second wire 462 is similarly connected to the components 452-456 opposite the first wire 460. The wires 460, 462 are aligned with one another and arranged such that the leading hub 454 can articulate relative to the distal-most hinge segment 452a (and vice-versa), adjacent ones of the hinge segments 452 can articulate relative to one another, and the proximal-most hinge segment 452b to the joiner hub 456 (and vice-versa). Finally, the wires 460, 462 are affixed to the leading hub 454 and the joiner hub 456, and thus retain the components 452-456 as a collective unit.

The wires 460, 462 can be formed of various, structurally robust materials (e.g., steel) and can be assembled to the corresponding components 452-456 in a variety of manners. For example, the leading hub 454 can form opposing pockets 470, 472 each open to a corresponding wire lumen 474, 476. As best shown in FIG. 10A, a crimp 480 is formed at, or attached to, a distal end of the first wire 460. The crimp 480 is sized and shaped to dock or lodge within the first pocket 470. Though not shown, a similar assembly is provided for the second wire 462 relative to the second pocket 472. The first wire 460 is then fed through the first wire lumen 474 (and the second wire 462 through the second wire lumen 476). First and second notches 490, 492 formed in the joiner hub 456 and fixedly receive a crimp 494 at a proximal end of the each of the wires 460, 462.

FIG. 10C illustrates one of the hinge segments 452 in greater detail. Commensurate with previous descriptions, the hinge segment 452 can form or provide opposing tabs 500, 502 and opposing grooves 504, 506. A central bore 508 is optionally provided, as is an optional pull wire lumen(s) 510. In addition, the hinge segment 452 forms a first wire lumen 512 through the first tab 500, and a second wire lumen 514 through the second tab 502. Upon stacked arrangement of a first one of the hinge segments 452 to a second one of the hinge segments 452 (e.g., in which the tabs 500, 502 of the first hinge segment 452 nest within the grooves 504, 506, respectively, of the second hinge segment 452), corresponding ones of the wire lumens 512, 514 will be aligned and can readily receive a corresponding one of the wires 460, 462 (FIGS. 10A and 10B). Construction of the deflection assembly 450 thus entails advancing the first wire 460 (otherwise attached to the leading hub 454 as described above) through the first wire lumen 512 of each of the aligned hinge segments 452, and advancing the second wire 462 through the second wire lumen 514. The crimp 494 is then attached to the proximal end of the first wire 460 and docked to the first notch 490 of the joiner hub 456 (and the crimp 494 attached to the proximal end of the second wire 462 is docked to the second notch 492).

With the above construction, the hinge region 458 can articulate or deflect in accordance with previous descriptions (e.g., in response to a compressive force applied to the leading hub 454 in a direction of the joiner hub 456). Further, when placed in tension (e.g., a distal pulling force applied to the leading hub 454 while the joiner hub 456 is held stationary), the wires 460, 462 prevent the deflection assembly 450 from pulling apart.

Figure 11A:
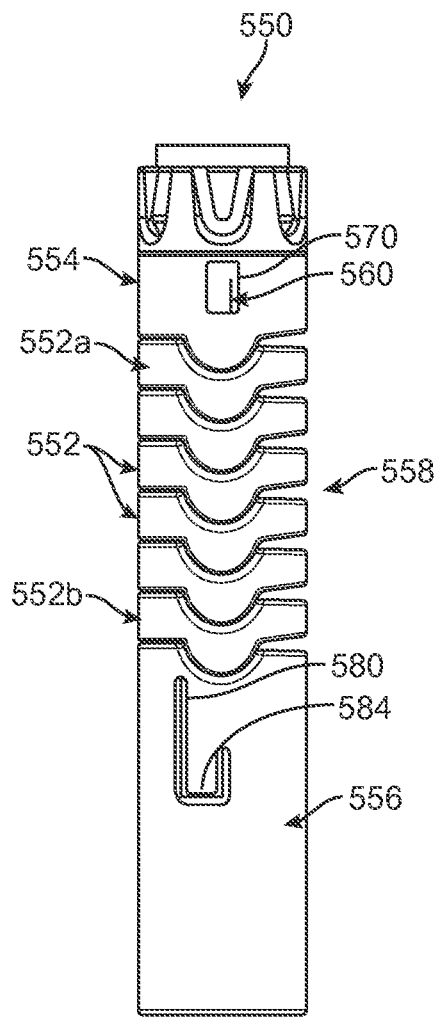
FIG. 11A is a side view of portions of another deflection assembly in accordance with principles of the present disclosure.
Figure 11B:
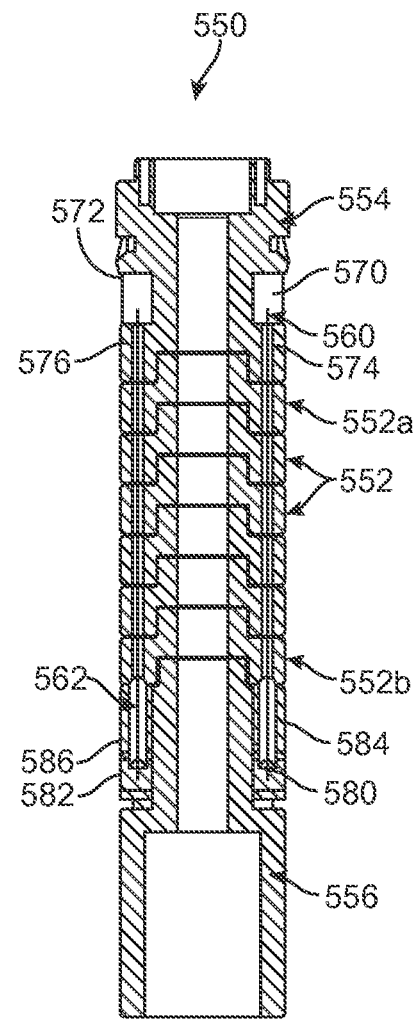
FIG. 11B is a cross-sectional view of the deflection assembly of FIG. 11A.

Portions of another embodiment deflection assembly 550 in accordance with principles of the present disclosure are shown in FIGS. 11A and 11B. The deflection assembly 550 includes a plurality of hinge segment 552, a leading hub 554, and a joiner hub 556. In general terms, the hinge segments 552 can be highly akin to the hinge segments 150 (FIG. 4), and can incorporate any of the features described above. Similarly, the leading hub 554 can be highly akin to the leading hub 152 (FIG. 4), and the joiner hub 556 can be highly akin to the joiner hub 154 (FIG. 4). Thus, an articulating interface is established between consecutive ones of the components 552-556 upon final assembly to collectively define a hinge region 558 as described above. In addition, the deflection assembly 550 includes one or more wires securing immediately adjacent ones of the components 552-556 to one another.

For example, FIG. 11A, illustrates a first wire 560 extending between the leading hub 554 and the joiner hub 556, and interconnected with each of the hinge segments 552. As generally reflected by FIG. 11B, a second wire 562 is similarly connected to the components 552-556 opposite the first wire 560. The wires 560, 562 are aligned with one another and arranged such that the leading hub 554 can articulate relative to the distal-most hinge segment 552a (and vice-versa), adjacent ones of the hinge segments 552 can articulate relative to one another, and the proximal-most hinge segment 552b to the joiner hub 556 (and vice-versa). Finally, the wires 560, 562 are affixed to the leading hub 554 and the joiner hub 556, and thus retain the components 552-556 as a collective unit.

Figure 11C:
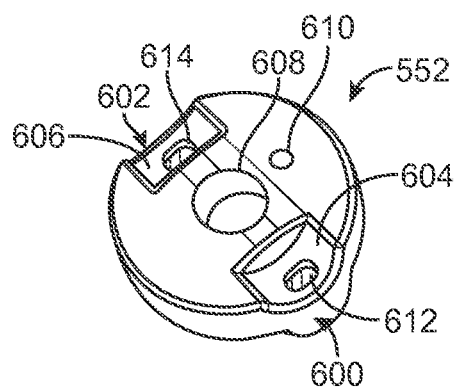
FIG. 11C is an enlarged perspective view of a hinge segment useful with the deflection assembly of FIG. 11A.

The wires 560, 562 can be formed of various, structurally robust materials (e.g., steel) and can be assembled to the corresponding components 552-556 in a variety of manners. For example, the leading hub 554 can form opposing pockets 570, 572 each open to a corresponding wire lumen 574, 576. The joiner hub 556 can include opposing slots 580, 582 that each generates a finger 584, 586. FIG. 11C illustrates one of the hinge segments 552 in greater detail. Commensurate with previous descriptions, the hinge segment 552 can form or provide opposing tabs 600, 602 and opposing grooves 604, 606. A central bore 608 is optionally provided, as is an optional pull wire lumen(s) 610. In addition, the hinge segment 552 forms a first wire lumen 612 through the first tab 600, and a second wire lumen 614 through the second tab 602. Upon stacked arrangement of a first one of the hinge segments 552 to a second one of the hinge segments 552 (e.g., in which the tabs 600, 602 of the first hinge segment 552 nest within the grooves 604, 606, respectively, of the second hinge segment 552), corresponding ones of the wire lumens 612, 614 will be aligned and can readily receive a corresponding one of the wires 560, 562 (FIGS. 11A and 11B).

Construction of the deflection assembly 550 can generally entail forming a knot or a crimp in the distal end of each of the wires 560, 562, and then docking the so-formed distal end in the corresponding pocket 570, 572 of the leading hub 554. Glue or other adhesive can optionally be applied to the loaded distal end to prevent the wire 560, 562 from unraveling. The first wire 560 is advanced through the first wire lumen 612 of each of the aligned hinge segments 552, and the second wire 562 is advanced through the second wire lumens 614. The first wire 560 is guided through the first slot 580 and secured against the first finger 584 of the joiner hub 556. The second wire 562 is similarly connected to the second finger 586. Glue or other adhesive can optionally be applied to further secure the wires 560, 562 to the corresponding finger 584, 586.

With the above construction, the hinge region 558 can articulate or deflect in accordance with previous descriptions (e.g., in response to a compressive force applied to the leading hub 554 in a direction of the joiner hub 556). Further, when placed in tension (e.g., a distal pulling force applied to the leading hub 554 while the joiner hub 556 is held stationary), the wires 560, 562 prevent the deflection assembly 550 from pulling apart.

The delivery devices, systems and methods of the present disclosure provide a marked improvement over previous designs. By providing the delivery device with a robust deflection assembly coaxially within the delivery sheath and immediately proximal the loaded stented prosthetic heart valve, the delivery device can be readily operated to effectuate desired bends or deflections commensurate with a desired delivery path presented by the anatomy of the particular procedure, even with more rigid or large outer sheath or catheter designs.

Although the present disclosure has been described with reference to preferred embodiments, workers skilled in the art will recognize that changes can be made in form and detail without departing from the spirit and scope of the present disclosure. For example, while the devices and systems of the present disclosure have been described as being useful for delivering a stented prosthetic heart valve, a number of other implantable devices can be employed.

What is claimed is:

1. A delivery device for implanting a stented prosthetic heart valve, the device comprising:
   an outer sheath;
   an inner shaft disposed within the outer sheath;
   a deflection assembly attached to the inner shaft and including:
   a plurality of stacked hinge segments, including a proximal-most hinge segment and a distal-most hinge segment, wherein each of the hinge segments are discretely formed as a solid body, wherein each of the hinge segments defines opposing, first and second major surfaces and have complimentary engagement features by which immediately adjacent ones of the hinge segments interface with, and can articulate relative to, one another, wherein the complimentary engagement features include a first tab and a first groove and further wherein the first tab is formed as a projection along the first major surface and the first groove is formed as a recess in the second major surface; wherein the first tab can slide within one adjacent first groove with respect to a central axis of the deflection assembly; further wherein each second major surface includes a platform region oriented generally perpendicular with respect to the central axis and each second major surface includes a spine; further wherein each spine represents a continuation of the second major surface from the platform region; further wherein the platform region is opposite the complimentary engagement features; further wherein the platform region tapers in thickness from the complimentary engagement features;
   a joiner hub connected to the inner shaft and interfacing with the proximal-most hinge segment,
   a leading hub interfacing with the distal-most hinge segment; and
   a support shaft attached to and extending distally from the leading hub;
   wherein the delivery device is configured to provide a loaded state in which a stented prosthetic heart valve is compressed over the support shaft and retained within a capsule of the outer sheath;
   and further wherein a hinge region of the deflection assembly is configured to be deflected by a user to change a spatial orientation of the support shaft relative to the inner shaft while the delivery device is in the loaded state.

2. The delivery device of claim 1, wherein each hinged segment further includes a second groove and the spine of each hinged segment is located between the first and second grooves.

3. The delivery device of claim 1, wherein the first tab is formed as a projection along the first major surface and the first groove is formed as a recess in the second major surface.

4. The delivery device of claim 1, wherein the plurality of stacked hinge segments further includes first and second intermediate hinge segments, and further wherein the first tab of the first intermediate hinge segment is nested within the first groove of the second intermediate hinge segment.

5. The delivery device of claim 1, wherein the first groove is open to a side of one hinge segment.

6. The delivery device of claim 1, wherein the complimentary engagement features further include a second tab and a second groove.

7. The delivery device of claim 6, wherein the first and second tabs are formed as projections along the first major surface, and the first and second grooves are formed as recesses in the second major surface.

8. The delivery device of claim 7, wherein the plurality of stacked hinge segments further includes first and second intermediate hinge segments, and further wherein the first and second tabs of the first intermediate hinge segment are nested within the first and second grooves, respectively of the second intermediate hinge segment.

9. The delivery device of claim 1, further comprising a first wire having opposing, first and second ends, wherein the wire extends through each of the hinge segments, and further wherein the first end is attached to the leading hub and the second end is attached to the joiner hub.

10. The delivery device of claim 1, wherein the deflection assembly is configured to be repeatedly translated between a linear arrangement and a deflected arrangement, and further wherein the linear arrangement includes a clearance gap being defined between immediately adjacent ones of the hinge segments at one side thereof.

11. The delivery device of claim 1, wherein the leading hub includes a valve retainer.

12. The delivery device of claim 11, wherein the valve retainer includes a first slot configured to receive a portion of a stent of a prosthetic heart valve.

13. The delivery device of claim 1, wherein the platform region is opposite the complimentary engagement features; wherein the platform region defines a clearance edge; wherein the clearance edge is arcuate to define an arc extending between first and second major surfaces.

14. A system for treating a defective heart valve, the system comprising:
 a delivery device comprising:
  an outer sheath,
  an inner shaft disposed within the outer sheath,
  a deflection assembly attached to the inner shaft and including:
   a plurality of stacked hinge segments, including a proximal-most hinge segment and a distal-most hinge segment, wherein each of the hinge segments are discretely formed as a solid body, wherein each of the hinge segments defines opposing, first and second major surfaces and have complimentary engagement features by which immediately adjacent ones of the hinge segments interface with, and can articulate relative to, one another, wherein the complimentary engagement features include a first tab and a first groove and further wherein the first tab is formed as a projection along the first major surface and the first groove is formed as a recess in the second major surface; wherein the first tab can slide within one adjacent first groove with respect to a central axis of the deflection assembly, further wherein each second major surface includes a platform region oriented generally perpendicular with respect to the central axis and each second major surface includes a spine; further wherein each spine represents a continuation of the second major surface from the platform region; further wherein the platform region is opposite the complimentary engagement features; further wherein the platform region tapers in thickness from the complimentary engagement features;
  a joiner hub connected to the inner shaft and interfacing with the proximal-most hinge segment,
  a leading hub interfacing with the distal-most hinge segment, and
  a support shaft attached to and extending distally from the leading hub,
  wherein a hinge region of the deflection assembly is configured to be deflected by a user to change a spatial orientation of the support shaft relative to the inner shaft while the delivery device is in a loaded state; and
 a prosthetic heart valve compressed over the support shaft and retained within a capsule of the outer sheath in the loaded state.

15. The system of claim 14, wherein the prosthetic heart valve is selectively secured to a valve retainer of the leading hub in the loaded state.

16. The system of claim 14, wherein the platform region is opposite the complimentary engagement features; wherein the platform region defines a clearance edge; wherein the clearance edge is arcuate to define an arc extending between first and second major surfaces.

* * * * *